United States Patent
Semen

(10) Patent No.: US 7,425,290 B2
(45) Date of Patent: *Sep. 16, 2008

(54) GRANULAR POLYMER ADDITIVES AND THEIR PREPARATION

(75) Inventor: John Semen, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 735 days.

This patent is subject to a terminal disclaimer.

(21) Appl. No.: 10/911,253

(22) Filed: Aug. 4, 2004

(65) Prior Publication Data

US 2005/0009725 A1    Jan. 13, 2005

Related U.S. Application Data

(60) Division of application No. 09/792,087, filed on Feb. 23, 2001, now Pat. No. 6,821,456, which is a continuation-in-part of application No. 09/528,675, filed on Mar. 20, 2000, now Pat. No. 6,800,228, which is a continuation-in-part of application No. 09/158,588, filed on Sep. 22, 1998, now Pat. No. 6,056,898, and a continuation-in-part of application No. 09/203,941, filed on Dec. 2, 1998, now Pat. No. 6,126,862, and a continuation-in-part of application No. 09/204,121, filed on Dec. 2, 1998, now Pat. No. 6,126,863.

(51) Int. Cl.
*B29C 67/00* (2006.01)
*B29C 67/02* (2006.01)
*C09K 15/08* (2006.01)

(52) U.S. Cl. .......... 264/109; 264/115; 264/118; 264/140; 264/141; 264/128; 264/122; 264/117; 264/143; 264/144; 264/145; 252/407; 252/400.24; 252/400.23; 252/182.29; 252/404

(58) Field of Classification Search .......... 252/404; 264/117
See application file for complete search history.

(56) References Cited

U.S. PATENT DOCUMENTS

| | | | |
|---|---|---|---|
| 3,664,961 A | 5/1972 | Norris | |
| 3,781,242 A * | 12/1973 | Mathis et al. | 524/83 |
| 3,781,397 A | 12/1973 | Gauer et al. | |
| 4,038,477 A | 7/1977 | Inoue et al. | |
| 4,077,902 A | 3/1978 | Moser et al. | |
| 4,098,858 A | 7/1978 | Ten Broeck | |
| 4,101,512 A | 7/1978 | Schmidt et al. | |
| 4,111,909 A | 9/1978 | Simons | |
| 4,134,725 A | 1/1979 | Buchel et al. | |
| 4,357,449 A | 11/1982 | Yi | |
| 4,438,263 A | 3/1984 | Morse | |
| 4,439,570 A | 3/1984 | Messina et al. | |
| 4,442,017 A | 4/1984 | Blumberg et al. | |
| 4,443,572 A | 4/1984 | Burns | |
| 4,446,086 A | 5/1984 | Molenaar et al. | |
| 4,510,073 A | 4/1985 | Hara et al. | |
| 4,560,527 A | 12/1985 | Harke et al. | |
| 4,594,444 A | 6/1986 | Orban | |
| 4,670,181 A | 6/1987 | Mollinger et al. | |
| 4,692,170 A | 9/1987 | Santambrogio et al. | |
| 4,716,244 A | 12/1987 | Orban | |
| 4,761,247 A | 8/1988 | Rei et al. | |
| 4,761,248 A | 8/1988 | Clift | |
| 4,764,428 A * | 8/1988 | Gloyer | 428/402 |
| 4,806,580 A | 2/1989 | Bock et al. | |
| 4,902,210 A | 2/1990 | Shibata | |
| 4,929,654 A | 5/1990 | Wang et al. | |
| 4,943,301 A | 7/1990 | Nagle et al. | |
| 4,956,406 A | 9/1990 | Myers et al. | |
| 4,957,956 A * | 9/1990 | Neri et al. | 524/120 |
| 5,006,284 A | 4/1991 | Gahan | |
| 5,011,640 A | 4/1991 | Zanchetta | |
| 5,030,400 A | 7/1991 | Danielsen et al. | |
| 5,117,040 A | 5/1992 | Marutani et al. | |
| 5,124,100 A | 6/1992 | Nishii et al. | |
| 5,153,029 A | 10/1992 | Sharma | |
| 5,190,579 A | 3/1993 | Gose et al. | |
| 5,196,565 A | 3/1993 | Ross | |
| 5,240,642 A * | 8/1993 | Neri et al. | 252/399 |
| 5,290,495 A | 3/1994 | Numadate et al. | |
| 5,292,461 A | 3/1994 | Juch et al. | |
| 5,318,733 A | 6/1994 | Carduck et al. | |
| 5,348,695 A | 9/1994 | Ploumen et al. | |
| 5,358,560 A | 10/1994 | Hitch et al. | |
| 5,382,377 A | 1/1995 | Raehse et al. | |
| 5,460,765 A | 10/1995 | Derdall et al. | |
| 5,462,984 A | 10/1995 | Neri et al. | |
| 5,597,857 A * | 1/1997 | Thibaut et al. | 524/400 |
| 5,606,007 A | 2/1997 | Sakashita et al. | |

(Continued)

FOREIGN PATENT DOCUMENTS

DE        1629732        3/1971

(Continued)

*Primary Examiner*—Joseph D Anthony
(74) *Attorney, Agent, or Firm*—Jeremy J. Kliebert

(57) ABSTRACT

A compacted particulate polymer additive composition in a dry granular form formed from a substantially uniform mixture of the following components:
(a) at least one particulate sterically-hindered phenolic compound; and
(b) one or more particulate polymer additives other than a sterically-hindered phenolic compound;
wherein the particles of said composition are held together in compacted dry granular form exclusively or substantially exclusively by contact with dried surfaces of in situ desolvated particles from particles of one or more at least partially solvated components of (a), and optionally by contact with dried surfaces of in situ desolvated particles from particles of one or more at least partially solvated components of (b). Compositions of this type except that there is no component (b) are also described.

20 Claims, No Drawings

U.S. PATENT DOCUMENTS

| | | |
|---|---|---|
| 5,614,571 A | 3/1997 | Mahood |
| 5,674,927 A | 10/1997 | Mahood |
| 5,700,497 A | 12/1997 | Stone et al. |
| 5,772,921 A | 6/1998 | Gilg et al. |
| 5,773,503 A | 6/1998 | Steen et al. |
| 5,844,027 A | 12/1998 | Burdick et al. |
| 5,844,042 A * | 12/1998 | Neri et al. .................. 523/223 |
| 5,846,656 A * | 12/1998 | Dunski ....................... 428/402 |
| 5,916,539 A | 6/1999 | Pilgrimm |
| 5,962,599 A | 10/1999 | Abe et al. |
| 5,997,768 A * | 12/1999 | Scully, Jr. ................ 252/367.1 |
| 6,033,600 A | 3/2000 | Henkins et al. |
| 6,056,897 A | 5/2000 | Pallini et al. |
| 6,056,898 A | 5/2000 | Semen |
| 6,077,890 A | 6/2000 | Hudson et al. |
| 6,126,862 A | 10/2000 | Semen |
| 6,126,863 A | 10/2000 | Semen |
| 6,143,814 A | 11/2000 | Schiller et al. |
| 6,515,052 B2 | 2/2003 | Semen |
| 6,596,198 B1 | 7/2003 | Semen |

FOREIGN PATENT DOCUMENTS

| | | |
|---|---|---|
| DE | 2922378 | 12/1980 |
| EP | 0 403 431 A2 | 12/1990 |
| EP | 0 514 784 A1 | 11/1992 |
| EP | 0 525 200 A1 | 2/1993 |
| EP | 0 719 824 A2 | 7/1996 |
| JP | 06254845 A2 | 9/1994 |
| WO | WO-97/09376 | 3/1997 |
| WO | WO-00/17267 | 3/2000 |
| WO | WO-01/70869 A2 | 9/2001 |

* cited by examiner

GRANULAR POLYMER ADDITIVES AND THEIR PREPARATION

REFERENCE TO RELATED APPLICATIONS

This application is a Division of commonly-owned application Ser. No. 09/792,087, filed Feb. 23, 2001 now U.S. Pat. No. 6,821,456, which is a continuation-in-part of commonly-owned application Ser. No. 09/528,675 filed Mar. 20, 2000, now U.S. Pat. No. 6,800,228, which in turn is a continuation-in-part of commonly-owned application Ser. No. 09/158,588 filed Sep. 22, 1998, now U.S. Pat. No. 6,056,898; Ser. No. 09/203,941 filed Dec. 2, 1998, now U.S. Pat. No. 6,126,862; and Ser. No. 09/204,121 filed Dec. 2, 1998, now U.S. Pat. No. 6,126,863.

TECHNICAL FIELD

This invention relates to the provision of improved polymer additives—i.e., additives which are for use in polymers—where the additives are in granular form such as pellets.

BACKGROUND

A wide variety of particulate additives are used in thermoplastic polymers in order to improve the properties of the polymer and/or the utility of products formed from such polymers. Included among the types of particulate polymer additives used are, for example, such substances as antioxidants, flame retardants, flame retardant synergists, thermal stabilizers, UV stabilizers, nucleating agents, acid neutralizers, polymer clarifiers, and the like. In order to facilitate blending operations it is desirable to provide additives in a granular form because many additives can cake up or form rat-holes in feed hoppers, and/or feed unevenly through metering equipment. Moreover, certain additives, especially finely-divided additives, often used in the manufacture of polymers, such as high melting nucleating agents and inorganic acid neutralizers can create hazardous airborne dusts during handling and blending operations.

Various methods for converting polymer additives into granular forms have been described heretofore. Such methods include melting at least one component of a dry blend of additives to thereby bond the particles of the blend together, or including in a blend of the additives a special component such as a wax, fatty acid, a compound containing a fatty acid chain or fatty alcohol chain, or metal salt of a fatty acid, and then converting the dry blend into granules or pellets by compacting or milling the blend. All such methods require use of extraneous components to serve as binders, which components are not necessarily desired as components in the finished polymer composition, and which may actually interfere with product specifications of the polymer producer. Moreover, use of some previously used binders can detract from performance properties of the host polymer. And, in some cases the scope of the additives that can be converted into granules or pellets is quite specific and thus not of widespread utility.

Some of these prior developments are described, for example, in U.S. Pat. Nos. 4,957,956; 5,240,642; 5,597,857; 5,844,042, 5,846,656; and 6,033,600.

It would be of considerable advantage if a way could be found of converting a blend of two or more particulate polymer additives into granular form such as pellets without depending upon melting a component of the blend or the binding action of a special binder component included in the powder blend such as a wax, a fatty acid, a compound containing a fatty acid chain or fatty alcohol chain, or metal salt of a fatty acid. It would be of even greater advantage if the scope of the blends of particulate additives converted into granules such as pellets could be broadened so that it is unnecessary to rely on only certain specific combinations of additives that produce granules.

This invention is deemed to accomplish these objectives in an efficient and effective manner.

BRIEF SUMMARY OF THE INVENTION

This invention makes it possible to provide granules of particulate polymer additives without use of conventional binder components and without relying on substantial melting of one or more components of the additive blend. In addition the invention is deemed to possess widespread utility in that a very large number of particulate polymer additives can be used in forming the granular additive compositions of this invention. Thus not only is it unnecessary to be restricted to use of specific combinations of additives but in addition, all of the components can be selected from components which are widely-used in thermoplastic polymers. This in turn makes it possible to avoid use of particular components which would be undesired or undesirable in the finished polymer product in which the granular additive composition is employed.

Thus, in one of its embodiments this invention provides a polymer additive composition consisting essentially of granules of dry compacted particles from the following components:

(a) at least one particulate sterically-hindered phenolic compound, and
(b) one or more particulate polymer additives other than a sterically-hindered phenolic compound, wherein the particles in said granules are held interbonded one to another in compacted dry granular form exclusively or substantially exclusively by interbonding with in situ desolvated surfaces of particles of one or more components of (a), and optionally by interbonding with in situ desolvated surfaces of particles of one or more components of (b). In other words, particles in these compositions are held together in compacted dry granular form exclusively or substantially exclusively by desolvated, dried, formerly at least partially-solvated particles of one or more components of (a), and optionally by desolvated, dried, formerly at least partially-solvated particles of one or more components of (b).

In another of its embodiments this invention provides a process of producing a compacted particulate polymer additive composition in a dry granular form, which process comprises:

1) forming a paste from (a) at least one particulate sterically-hindered phenolic compound, (b) one or more particulate polymer additives other than a sterically-hindered phenolic compound, and (c) an inert organic processing solvent that can be temperature of (a) and (b);
2) compressing and shaping the paste while preventing or substantially preventing melting of solids used in forming the paste, to produce a wet compacted composition in granular form; and
3) drying said wet compacted composition in granular form by vaporizing said processing solvent therefrom to form the dried compacted particulate polymer additive composition in a granular form.

Typically a compression apparatus operated so as to prevent or substantially prevent melting of solids is used in conducting step 2) of the process.

An optional further step that maybe used is to screen or otherwise classify the dried granular product mixture to separate from the granular product fine particles, if any, that may be present. Such fine particles may be recycled as a feed to the process.

Still another of the embodiments of this invention is a compacted particulate polymer additive composition in a dry granular form, formed by a process which comprises:

1) forming a paste from a substantially uniform mixture of (a) at least one particulate sterically-hindered phenolic compound, (b) one or more particulate polymer additives other than a sterically-hindered phenolic compound, and (c) an inert organic processing solvent that can be vaporized at a temperature below the lowest melting point or initial melting temperature of (a) and (b);
2) compressing and shaping the paste while preventing or substantially preventing melting of solids used in forming the paste, to produce a wet compacted composition in granular form; and
3) drying said wet compacted composition in granular form by vaporizing said processing solvent therefrom to form said additive composition in a dry granular form;

said additive composition having compressive hardness and physical integrity resulting from the particles in said granules being held interbonded one to another in compacted dry granular form exclusively or substantially exclusively by interbonding with in situ desolvated surfaces of particles of one or more components of (a), and optionally by interbonding with in situ desolvated surfaces of particles of one or more components of (b). In other words, the resultant composition has compressive hardness and physical integrity resulting exclusively or substantially exclusively from desolvated, dried, formerly at least partially solvated particles of (a), and optionally from desolvated, dried, formerly at least partially solvated particles of (b).

Other embodiments and features of this invention will be still further apparent from the ensuing description and appended claims.

FURTHER DETAILED DESCRIPTION OF THE INVENTION

As used herein, including the claims, the phrase "wherein the particles in said granules are held interbonded one to another in compacted dry granular form exclusively or substantially exclusively by interbonding with in situ desolvated surfaces of particles of one or more components of (a), and optionally by interbonding with in situ desolvated surfaces of particles of one or more components of (b)" means that the granules are held together in compacted dry form entirely or almost entirely by dried particles of one or more components of (a) that now are desolvated but which were at least partially solvated when the granules were dried in situ, and optionally also by dried particles of one or more components of (b) that now are desolvated but which were at least partially solvated when the granules were dried in situ. If component (a) happens to be, say, two different components meeting the definition of (a), dried particles of only one such component of (a) that now are desolvated but which were at least partially solvated when they were dried need hold the granules in compacted dry granular form. The other such component of (a) need not have been solvated to any extent. However, dried particles of the two such components of (a) that now are desolvated but which were at least partially solvated when they were dried can be holding the granules in compacted dry granular form. In any such case it is optional whether particles of one or more components of (b) were or were not solvated to any extent, or if they were at least partially solvated, whether they contribute in any way to holding the granules in compacted dry granular form. However, dried particles of component (b) that now are desolvated but which were at least partially solvated when they were dried may be contributing to holding the granules in compacted dry granular form, since such contribution by particles of (b) to the holding of the granules in compacted dry granular form is optional.

It will be seen that no component of the additive blends processed pursuant to this invention is caused to be melted during the process. Instead a wet paste formed from particulate solids and an inert organic processing solvent is compressed, preferably in a compression apparatus, and the compression is conducted so as to substantially prevent melting of the solids used in forming the paste.

In addition it will be seen that the particles in the granules are held together not by a conventional binder such as a wax, a paraffin, a fatty acid, a compound containing a fatty acid chain or fatty alcohol chain, or metal salt of a fatty acid. Instead, the binding action in the granules results entirely or substantially entirely from the drying of solvated or partially solvated component (a) above, viz., the particulate sterically-hindered phenolic compound(s) used, and optionally from the drying of one or more solvated or partially solvated particulate components of (b) used in forming the granules.

As those of ordinary skill in the art will readily appreciate from a reading of this disclosure, not all particles of (a) above need be solvated or partially solvated when forming the granules of this invention. It will suffice if a sufficient number of the particles of (a) above dispersed within the paste are solvated or partially solvated and then compressed and dried in contact with other particles in the granules to hold the granules together and provide granules having sufficient compressive hardness and physical integrity to be used in conventional polymer additive blending apparatus. These same considerations apply to the extent, if any, that particles of (b) are solvated or partially solvated and contribute to the binding action that holds the particles together in the form of granules having such properties—not all such particles of (b) need be solvated or partially solvated nor contribute to the binding action. Those of ordinary skill in the art will also readily appreciate after reading this disclosure that not every single particle in the finished granules of this invention need be bound together. Instead, a suitably small number of free particles may simply be encased or entrapped within a network of bonded particles throughout the granule. Naturally there must be a sufficient number of suitably bonded particles to confer and maintain the compressive hardness and physical integrity enabling the granules to be used in conventional polymer additive blending apparatus.

It will also be readily appreciated by those of ordinary skill in the art from a reading of this disclosure and the application of reason and common sense, that if two or more different sterically-hindered phenolic compounds are used as component (a) above it is not necessary that all such components of (a) contribute to the binding action. It will suffice if just one such component provides the necessary binding action and is present in an amount sufficient to result in the formation of dried finished granules of compressive hardness and physical integrity enabling the granules to be used in conventional polymer additive blending apparatus.

Among the advantageous features of this invention is that sterically-hindered phenolic compounds are known to be very useful as antioxidants and in some cases, such as 2,2'-methylenebis[6-(2H-benzotriazol-2-yl)-4-(1,1,3,3-tetramethylbutyl)phenol, as UV stabilizers. In fact various stericallyhindered phenolic compounds are widely used in actual practice as polymer additives. Thus the sterically-hindered phenolic compounds used are desirable additive components which serve at least two functions: (1) providing binding strength on desolvation, compression and/or drying and (2) providing antioxidant or other protection to the finished polymer in which the granules are ultimately used.

Without being bound by theory, the available evidence indicates that at least a portion of the particulate sterically-hindered phenolic component in the paste dissolves in the processing solvent to thereby form or act as a glue or adhesive which serves as a result of the compression and/or drying to bind the additive particles together. In other words, it appears that the particles in the dry compacted granules are held together in compacted dry granular form exclusively or substantially exclusively by desolvated adhesive from at least partially solvated particles of the sterically-hindered phenolic component(s) used in forming the granular additive composition. In some of the granular compositions of this invention it is possible that in addition to bonding due to desolvated residues of component (a) above, a portion of the bonding is the result of desolvated residues from one or more of the polymer additives of (b) above. To the extent, if any, that such optional bonding from (b) occurs in addition to the bonding from desolvated residues from (a), such co-bonding is within the scope of this invention provided that the physical integrity of the granules is due in such case substantially exclusively to the binding action of dried glue(s) or adhesive(s) formed from desolvated residue(s) from the sterically-hindered phenolic compound(s) of (a) and desolvated residue(s) from one or more of the polymer additives of (b) above. Such residues, if they form, may be separate individual residues or they may be mixed residues, or a combination of one or more separate individual residues and of one or more mixed residues. In short, the chemical constitution of co-binding glue(s) or adhesive(s), if any, from desolvation matters not, provided that substantial bonding results from (a), and that any such glue(s) or adhesive(s) bind the particles together one to another upon compression and/or drying to form granules with compressive hardness and physical integrity.

The term "substantially exclusively" as used herein denotes that the physical integrity of the granules is due at least mainly or principally (i.e., the highest in degree) to the binding action of compressing and/or drying solvated particles formed (i) solely from the stericallyhindered phenolic compound(s) of (a) used in forming the granules, or (ii) from both the steric ally-hindered phenolic compound(s) of (a) and one or more of the components of (b) used in forming the granules. As shown hereinafter, granules of desirable compressive hardness and physical integrity can be formed by the practice of this invention without use of any component known in the art to be a binder irrespective of the mechanism by which it functions. In fact, granules of desirable compressive hardness and physical integrity were made using a sterically-hindered phenolic compound as the sole particulate component of the paste formed and used in the processing of this invention. Thus in the practice of this invention bonding due to melting or plastic deformation of a component that in its original state is tacky or pliable, if any such melting or plastic deformation occurs, is incidental and minimal.

As is well known in the art, sterically-hindered phenolic compounds are characterized by having a sterically-hindering organic substituent in at least one of the ortho positions relative to a hydroxyl group on an aromatic ring. Such sterically-hindering group can be a hydrocarbyl group or a organic group containing one or more hetero atoms, typically nitrogen or oxygen atoms. Usually the sterically-hindering group(s) will contain at least 4 carbon atoms in a branched configuration especially as $C_4$ or higher tertiary alkyl group, such as tertbutyl, tert-amyl, 1,1,3,3-tetramethylbutyl group or as a cyclic organic group having at least 5 atoms in a ring, such as a cyclopentyl, cyclohexyl, or phenyl group.

The amount of the sterically-hindered phenolic component(s) can be relatively small in relation to the other particulate additive components used in forming the granules. Thus although the granular additives produced pursuant to this invention can contain as much as about 95 wt % of one or more particulate sterically-hindered phenolic components, the dry compacted granular additive compositions of this invention preferably contain no more than about 50 wt %, more preferably in the range of about 3 to about 40 wt %, still more preferably in the range of about 5 to about 30 wt %, and most preferably in the range of about 15 to about 30 wt % of one or more such sterically-hindered phenolic compounds, the balance to 100 wt % being one or more other kinds of particulate additives, such as for example, phosphorus-containing secondary antioxidants or stabilizers, amine antioxidants, thermal stabilizers, flame retardants, flame retardant synergists, UV stabilizers, nucleating agents, acid neutralizers, polymer clarifiers, and so on.

In order to prevent any substantial melting from occurring during the preparation of the granular compositions of this invention, it is preferred that each particulate component used in forming the granules have a melting point or initial melting temperature of at least about 50° C., more preferably at least about 100° C., and most preferably at least about 150° C. Consistent with this, the processing solvent used will be an inert organic solvent that can be vaporized, preferably at ordinary atmospheric pressure, at a temperature below the lowest melting point or initial melting temperature of the mixture of the particulate components. Because all operations used in forming the granular or pelleted compositions of this invention are conducted so as to substantially prevent melting of any additive component used in forming such compositions, adhesion due to melting is not utilized for bonding the particles together. Nor is bonding of particles due to plastic deformation of an initially tacky or pliable component involved since no component known to function in such a way need be present in the mixture being processed pursuant to this invention.

The particle size of the particulate components used in forming the paste from which the granular additive compositions of this invention are prepared is not critical as long as the particles are not so large as to be as large or larger than the granules or pellets to be produced. Thus the term "particulate" as used herein refers to particles that can range from fine powders to small grains in size—in short, any particle size which can be converted into the granules of the desired size.

Granules formed pursuant to this invention can be of any size suitable for use in conventional additive blending apparatus or additive feeding equipment used in connection with polymer blending and/or molding or extrusion operations. In addition, the granules can be in any of a variety of suitable shapes such as cylindrical pellets, spherical pellets, tablets, or flakes. And the granules, whatever their shape and size, should be free-flowing, non-sticky and free of appreciable dust-forming characteristics. Preferred granules of this invention have a compressive hardness of at least about 10 pounds per inch as measured by a test procedure described hereinafter.

The sterically-hindered phenolic compounds of (a) above used in the practice of this invention include mononuclear phenolic compounds and polynuclear phenolic compounds which preferably have melting points or initial melting temperatures of at least about 50° C. The initial melting temperature is of course applicable to a component that has a melting range as distinguished from a melting point, the initial melting temperature thus being the lowest temperature at which melting begins in a component that melts over a temperature range. Many highly suitable sterically-hindered phenolic compounds are available in the marketplace. Among suitable sterically-hindered phenolic compounds with melting points or initial melting temperatures of at least about 50° C. are such compounds as:

2-tert-butyl-4-methylphenol;
2,6-di-tert-butyl-4-methylphenol;
2,6-di-tert-butyl-4-methoxyphenol;
2-tert-butylhydroquinone;
2-phenylphenol;
2,6-diphenylphenol;
1-isopropyl-2-naphthol;
2-isopropyl-1-naphthol;
1-tert-butyl-2-naphthol;
2-tert-butyl-1-naphthol;
2,2'-methylenebis(6-tert-butyl-4-methylphenol);
2,2'-methylenebis(6-tert-butyl-4-ethylphenol);
4,4'-methylenebis(2,6-di-tert-butylphenol);
2,6-di-tert-butyl-N,N-dimethylamino-p-cresol;
2,2'-methylenebis[6-(2H-benzotriazol-2-yl)-4-(1,1,3,3-tetramethylbutyl)phenol;
1,3,5-trimethyl-2,4,6-tris(3,5-di-tert-butyl-4-hydroxybenzyl)benzene;
tris(3,5-di-tert-butyl-4-hydroxybenzyl)isocyanurate;
crystalline tetrakis[3-(3,5-di-tert-butyl-4-hydroxyphenyl)propionyloxymethyl]emthane;
2-tert-butyl-6-(3-tert-butyl-2-hydroxy-5-methylbenzyl)-4-methylphenyl acrylate;
2,4-bis(n-octylthio)-6-(4-hydroxyl-3,5-di-tert-butylanilino)-1,3,5-triazine;
1,6-hexanediylbis(3,5-di-tert-butyl-4-hydroxyphenylpropionate);
2,2'-ethylidenebis(4,6-di-tert-butylphenol);
n-octadecyl-3-(3',5'-di-tert-butyl-4-hydroxyphenyl)propionate;
2,2-bis[3',5'-di-tert-butyl-4'-hydroxyphenylpropionyloxyethoxyphenyl]propane;
1,2-ethanediylbis(oxy-2,1-ethanediyl)-3-tert-butyl-4-hydroxy-5-methylphenylpropionate (a.k.a. triethyleneglycol-bis[3-(3'-tert-butyl-4'-hydroxy-5-methylphenyl)propionate); and
1,5-bis(3',5'-di-tert-butyl-4'-hydroxyphenylpropionyloxy)-3'-thiopentane.

Sterically-hindered phenolic compounds typically are compounds containing in the molecule at least one hydroxyphenyl group in which at least one of the carbon atoms in the ortho-position relative to the hydroxyl group contains a substituent containing at least 3 and more preferably at least 4 carbon atoms. Oftentimes the two carbon atoms in the ortho-positions relative to such hydroxyl group contain a substituent, at least one of which contains at least 3 and more preferably at least 4 carbon atoms. Such ortho-substituted hydroxyphenyl moiety is often, but not necessarily, bonded to another carbon atom (e.g., as a 2,6-dialkyl-4-hydroxybenzyl group), as for example in the cases of the 2,6-dialkyl-4-hydroxybenzyl-substituted amines described in U.S. Pat. No. 2,962,531, the 2,6-dialkyl-4-hydroxybenzyl-substituted trialkylbenzenes described in U.S. Pat. No. 3,026,264, and the 2,6-dialkyl-4-hydroxybenzyl-substituted isocyanurates described in U.S. Pat. No. 3,531,483, each of which patent disclosures is incorporated herein by reference. If not bonded to another carbon atom the 2,6-dialkyl-4-hydroxyphenyl moiety can be bonded, for example, to a hydrogen atom, as in the case 2-methyl-6-(1,1,3,3-tetramethylbutyl)phenol, or to some other non-carbon atom, such as an oxygen atom, a nitrogen atom, a phosphorus atom, etc., as part of a larger molecule, e.g., as part of an ether, an amine, or an esterified acid of trivalent or pentavalent phosphorus. More preferred are compounds containing at least one hydroxyphenyl group in the molecule in which at least one of the ortho-positions relative to the hydroxyl group is substituted by a tertiary alkyl group. Still more preferred are compounds containing at least one hydroxyphenyl group in which each of the ortho-positions relative to the hydroxyl group is substituted by a tertiary alkyl group such as a tertiary butyl group.

Examples of some of the preferred compounds are as follows:

A. Octadecyl 3,5-di-t-butyl-4-hydroxyhydrocinnamate having the structure:

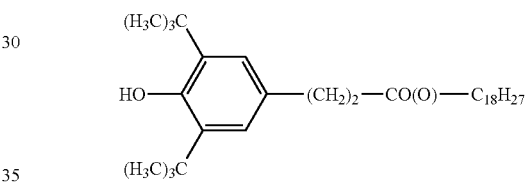

which has a melting point of 50-55° C. (122-131° F.) and is a product of Ciba Special Chemicals of Tarrytown, N.Y., and available under the trade name Irganox 1076;

B. Tetrakis [methylene(3,5-di-t-butyl-4-hydroxylhydrocinnamate)]methane having the structure:

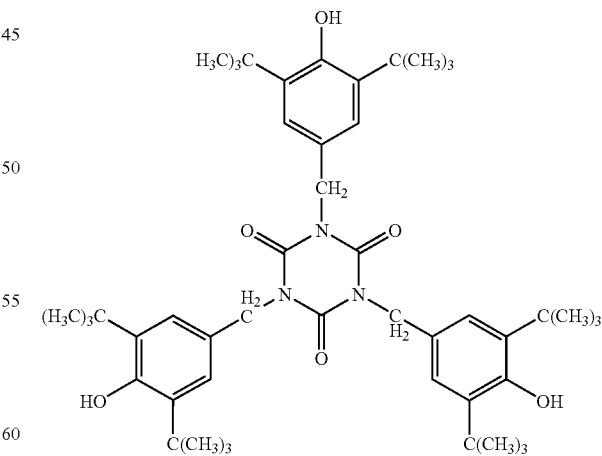

which has a melting point of 110-125° C. (230-257° F.) and is a product of Great Lakes Chemical Corporation of West Lafayette, Ind., or Ciba Specialty Chemicals of Tarrytown, N.Y., and available under the trade name Anox 20 or Irganox 1010, respectively;

C. 1,3,5-tris-(3,5-di-t-butyl-4-hydroxybenzyl) isocyanurate having the structure:

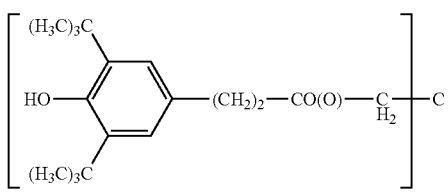

which has a melting point of 218-224° C. (424.5-433.5° F.) and is a product of Albemarle Corporation of Richmond, Va., and available under the trade name Ethanox® 314 antioxidant or Ciba Specialty Chemicals of Tarrytown, N.Y., and available under the trade name Irganox 3114;

D. 1,3,5-tris-(4-t-butyl-3-hydroxy-2,6-dimethylbenzyl)-1,3,5-triazine-2,4,6-(1H,3H, 5H)-trione having the structure:

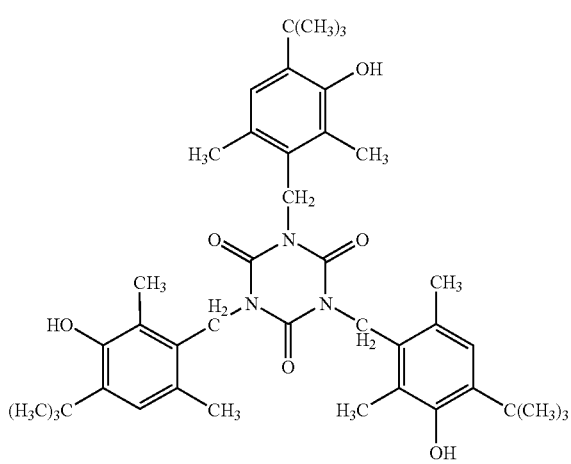

which has a melting point of 155-159° C. (311-318° F.) and is a product of Cytec of Stamford, Conn., and available under the trade name Cyanox 1790;

E. Thiodiethylenebis-(3,5-di-t-butyl-4-hydroxy) hydrocinnamate having the structure:

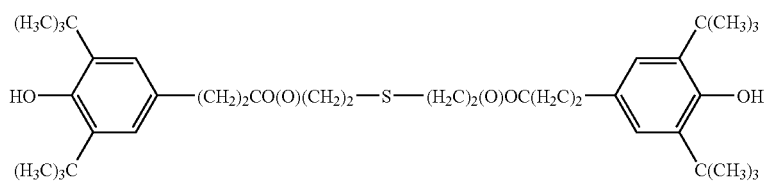

which is a product of Ciba Specialty Chemicals of Tarrytown, N.Y., which has a melting point of about 63° C. (145° F.), and is available under the trade name Irganox 1035; and, F. 1,3,5-trimethyl-2,4,6-tris-(3,5-di-tert-butyl-4-hydroxybenzyl)benzene having the structure:

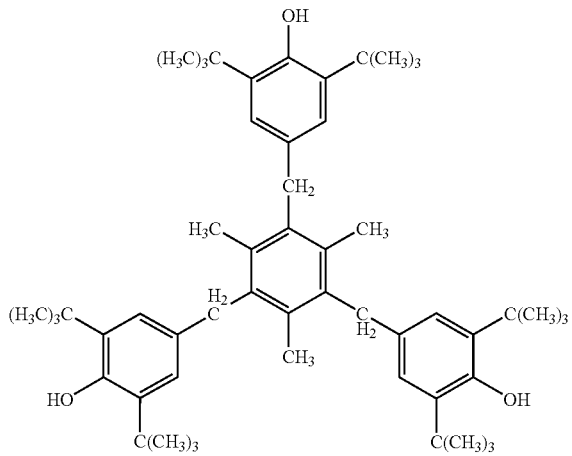

which has a melting point of 244° C. (471° F.) and is a product of Albemarle Corporation of Richmond, Va., and available under the trademark Ethanox 330 antioxidant.

Of these preferred sterically hindered phenolic compounds, 1,3,5-trimethyl-2,4,6-tris(3,5-di-tert-butyl-4-hydroxybenzyl)benzene and 1,3,5-tris-(3,5-di-t-butyl-4-hydroxybenzyl) isocyanurate are most preferred.

For ease of reference, the sterically-hindered phenolic compounds used as component (a) herein are sometimes referred to hereinafter, whether used singly or as a combination of two or more such compounds, as "phenolic component".

Any of a vast number of particulate polymer additive can be used as component(s) of (b) above—i.e., one or more particulate additives other than one or more components of (a) above. The criteria to be used in selecting one or more components of (b) above are that the component be a particulate additive having a melting point or initial melting temperature above the boiling point or final boiling temperature of the processing solvent and above the highest temperature to which the mixture of (a) and (b) will be exposed during the mixing, compressing and drying steps, (preferably a melting point or initial melting temperature of at least about 50° C., more preferably at least about 100° C., and most preferably at least about 150° C.), that it not be a tacky or pliable substance to which other particulate substances will stick or embed to any significant extent during processing, for example by plastic deformation under pressure, and that it be suitable for use as an additive to improve the processability, properties, and/or performance of the finished polymer in which it is employed.

Thus in general the particulate additive(s) used as component (b) should be a free-flowing particulate additive that will not melt under the particular conditions selected for use in compressing and drying the paste. Among the categories of polymer additives that can be used are non-phenolic antioxidants, UV or light stabilizers, nucleating agents, acid neutralizers, polymer clarifiers, flame retardants, flame retardant synergists, fillers and reinforcing agents, metal deactivators or passivators, as well as various other functional additives. The art is replete with information about such polymer additives that satisfy these criteria, and thus little would be gained by burdening this disclosure with enormous listings of such additives. A recent patent, U.S. Pat. No. 6,060,543, provides a more-than-adequate listing of typical polymer additives from which components meeting the foregoing criteria can be selected. Thus suitable non-sterically-hindered antioxidants—as well as sterically-hindered phenols which may be considered for use as component (a)—can be found within the disclosure of that patent from Column 34, line 28 through Column 37, line 35. From Column 37, line 36 through Column 40, line 2 of that patent is a listing of UV absorbers and light stabilizers from which components meeting the foregoing criteria can be found. Suitable metal deactivators or passivators can be found in the disclosure of that patent in Column 40, lines 3-12. The patent at Column 42, lines 31 through 38 lists nucleating agents, and at Column 42 from lines 39 through 43 lists fillers and reinforcing agents, from which components of these types meeting the above criteria can be selected. Suitable thiosynergists, peroxide scavengers, polyamide stabilizers, and basic co-stabilizers can be found within the listings at Column 41, lines 49 through 67, and Column 42, lines 29 and 30 of the patent. All of these passages of the patent are incorporated herein by reference with the caveat that each component that is selected from such listings must meet the foregoing criteria.

A few non-limiting examples of types of additives of component (b) that can be used in forming the compositions of this invention include:

A) Phosphorus-containing stabilizers or secondary antioxidants including, for example, organic phosphites such as are described in U.S. Pat. Nos. 4,094,855; 4,929,654; or 4,956,406; organic phosphonites such as are described in U.S. Pat. No. 4,233,207 or 4,912,155; and organic phosphonates such as are described in U.S. Pat. No. 3,737,486 or 4,524,167, each such patent being incorporated herein by reference. A few specific non-limiting examples of suitable organic phosphorus compounds that can be used include tris(2,4-di-tert-butylphenyl)phosphite; bis(2,4-di-tert-butylphenyl)pentaerythritol diphosphite; tetrakis(2,4-di-tert-butylphenyl)-4,4'-biphenylenediphosphonite; 2,4,6-tri-tert-butylphenyl-2-butyl-2-ethyl-1,3-propanediol phosphite; ethylbis(2,4-di-tert-butyl-6-methylphenyl)-phosphite; 3,9-bis(2,4-di-tert-butyl-4-methylphenoxy)-2,4,8,10-tetraoxa-3,9-diphosphaspiro[5.5]undecane; 3,9-tris(2,4,6-tris-tert-butylphenoxy)-2,4,8,10-tetraoxa-3,9-diphosphaspiro[5.5]undecane; 2,2'-ethylidenebis(4,6-di-tert-butylphenyl)fluorophos-phonite; 2,2',2"-nitrilo[triethyl-tris(3,3',5,5'-tetra-tert-butyl-1,1'-biphenyl-2,2'-diyl)]phosphite; bis(2,6-di-tert-butyl-4-carbomethoxyphenyl)phosphorochlorodite; bis(2,6-di-tert-butyl-4-carbo-2',4'-di-tert-butylphenoxyphenyl) phosphorochlorodite; bis(2,6-di-tert-butyl-4-ethylcarbomethoxyphenyl)phosphorochlorodite; 4,4-dimethyl-2,6-dioxaphosphite of 2,4-di-tert-butylphenyl-3,5-di-tert-butyl-4-hydroxybenzoate; cyclic ethylene phosphite of 2,4-di-tert-butylphenyl-3,5-di-tert-butyl-4hydroxybenzoate; cyclic ethylene phosphite of noctyl-3,5-di-tert-butyl-4-hydroxybenzoate; O-acetylbis(2,6-di-tert-butyl-4-carbomethoxyphenyl ester)phosphite; bis(2,6-di-tert-butyl-4-carbomethoxyphenyl ester)phosphonic acid; O-(2,6-di-tert-butyl-4-methylphenyl)phenylphosphonochloridite; O-(2,6-di-tert-butyl-4-methylphenyl)O'-(2,4-di-tert-butylphenyl)phenylphosphonite; O-(2,4-di-tert-butylphenyl)-O'-(2,4,6-tri-tert-butylphenyl) phenylphosphonite; O-(2,6-di-tert-butyl-4-methylphenyl)-O'-(2,6-di-tert-butyl-4-carbomethoxyphenyl)phenylphosphonite; O-(2,4,6-tri-tert-butylphenyl)phenylphosphonite; O,O'-bis(2,6-di-tert-butyl-4-carbomethoxyphenyl)phenylphosphonite; and bis(2,4-dicumylphenyl)pentaerythritol diphosphite. Mixtures of two or more such compounds can be used, if desired. Preferred phosphorus additives are tris(2,4-di-tert-butylphenyl)phosphite (mp ca. 182-188° C.) and bis(2,4-di-tert-butylphenyl)pentaerythritol diphosphite (mp ca. 160-175° C.), with tris(2,4-di-tert-butylphenyl)phosphite being most preferred.

B) One or more particulate sterically-hindered amine stabilizers such as bis(2,2,6,6-tetramethyl-4-piperidinyl)sebacate, bis(2,2,6,6-tetramethyl-4-piperidinyl)succinate, and similar stabilizers meeting the above criteria selected from the stabilizers identified in the passage from Column 4, line 29 through Column 23, line 36 of U.S. Pat. No. 5,597,857, which passage is incorporated herein by reference.

C) One or more particulate nucleating agents such as for example sodium 2,2'-methylenebis(4,6-di-tert-butylphenyl)phosphate, sodium adipate, sodium diphenylacetate, and sodium benzoate. Sodium benzoate is a preferred nucleating agent.

D) One or more particulate polymer clarifiers such as for example 1,3:2,4-bis(3,4-dimethylbenzylidene)sorbitol (Millad 3988; Millikan Chemical), 1,3:2,4-bis-(p-methylbenzylidene)sorbitol (Millad 3940; Millikan Chemical), and 1,3:2,4-di-O-benzylidenesorbitol (Millad 3905; Millikan Chemical).

E) One or more particulate acid neutralizers such as for example metal oxides (e.g., zinc oxide, magnesium oxide, and titanium dioxide), metal carbonates (e.g., calcium carbonate, and magnesium carbonate) and natural or synthetic hydrocalcites (e.g., magnesium hydrotalcites such as DHT-4A, DHT-4V, DHT-4C (all available from Kyowa Chemical Co.); Hysafe 539 and Hysafe 530 (available from J.M. Huber Corporation); L-55R acid neutralizers (available from Reheis Inc.); and zinc hydrotalcites such as ZH4-A (available from Kyowa Chemical Co.). Preferred acid neutralizers are DHT-4A, DHT-4V and DHT-4C.

F) One or more particulate flame retardants, such as decabromodiphenyl oxide, tetrabromobisphenol-A, hexabromocyclododecane, SAYTEX 801 flame retardant, a brominated aromatic compound of proprietary structure (Albemarle Corporation), tetradecabromodiphenoxybenzene, tetrabromocyclo-octane, ethylenebistetrabromo-phthalimide, bis(2,3-dibromopropyl ether) of tetrabromobisphenol-A, bis(2,3-dibromopropyl ether) of tetrabromobisphenol-S, hexabromobenzene, melamine, ammonium polyphosphate, and particulate organic phosphorus flame retardants, such as high-melting nitrogen-containing diphosphinic compounds such as described in U.S. Pat. No. 5,281,637, the disclosure of which pertaining to such compounds and their preparation is incorporated herein by reference.

G) One or more particulate flame retardant synergists, such as antimony tnoxide, sodium antimonate, and sodium borate.

H) One or more particulate heat stabilizers, such as dibutyltin mercaptopropionate (Barostab M 36; Barlocher (3 mbH), dioctyltin mercaptopropionate (Barostab OM 36; Barlocher GmbH), and polymeric dibutyltin maleate (Barostab MS; Barlocher GmbH).

I) One or more particulate fillers or reinforcing agents, such as silica, alumina, silica alumina, natural or synthetic zeolite, montmorillonite, short glass fibers, and metal whiskers.

A binding quantity of the phenolic component is used in forming the granulated products of this invention, i.e., an amount which upon completion of the drying step is enough to provide granules having sufficient compressive hardness and physical integrity to withstand conventional handling, transporting, and mixing operations used in forming dry polymer blends for use in molding or extrusion of molten polymer blends. It is preferable to provide a content of the phenolic component of at least about 3 wt % in the dried granulated product. More preferable is a content of the phenolic component of at least about 5 wt %, and still more preferable is a content of at least about 10 wt %. Most preferably the content of the phenolic component of is at least about 15 wt %.

The processing solvent used is preferably one in which the phenolic component used has a minimum solubility of about 5 grams per liter of solvent. More preferably, at the temperature of paste formation, the minimum solubility of the phenolic component in the solvent is about 10 grams per liter of solvent, and most preferably is about 20 grams per liter of solvent. Preferably, however, the solvent used is one in which the solubility of the phenolic component is limited. Thus, it is desirable to use a solvent in which the phenolic component has a maximum solubility of about 300 grams of phenolic component per liter of solvent, with a maximum solubility of about 200 grams per liter being more desirable, and a maximum solubility of about 100 grams per liter being most desirable. Such solubilities are preferably measured at a temperature in the range of from about 20° C. to about 70° C., but most preferably are measured at the temperature at which the paste is formed into granules.

It should be noted that even when using phenolic component/processing solvent pairs in which the solubilities which are greater than the maximum values given above, it is possible, in principle, to form granules or pellets according to the process of this invention. Adjustment of the solvent level can be performed, in most cases, to yield a suitable paste.

To form the paste, it is preferable to dry blend each of the particulate components of (a) and (b) together in a dry blender to form a substantially uniform mixture, and then to add the processing solvent and mix the resultant wet mixture to form a substantially uniform paste. However, other modes of addition can be used. For example, when forming a mixture which is to be granulated, such as a mixture of a phenolic component, a high melting acid neutralizer and a high melting nucleating agent, and the processing solvent, it is not necessary to combine the dry components before adding the processing solvent. Instead, the acid neutralizer can be mixed with the nucleating agent to form a mixture to which the solvent, and phenolic component are added, concurrently or in any order. If desired, one of the dry components can be combined with the processing solvent, followed by the addition of the other two dry components. Still another approach is to continuously combine the ingredients in small amounts immediately prior to granulation. In short, there is nothing critical about the order or mode of addition; any method which results in the formation of a substantially uniform paste can be used.

Regardless of order or mode of addition, it is preferable to evenly disperse the phenolic component with the other particulate component(s) so that the phenolic component is substantially uniformly dispersed within the paste before the granulation process.

If the paste which is to be formed will comprise one or more acid neutralizer, polymer clarifiers and/or nucleating agent components, it is highly preferable that the phenolic component be soluble in the processing solvent at the paste formation temperature. If any other particulate components are soluble in the processing solvent at paste formation temperature, such solubility will not necessarily decrease the compressive hardness of the resulting granules.

Furthermore, if the phenolic component used is a mixture or combination of two or more sterically-hindered phenolic compounds, low dust compositions of the present invention can be prepared if even only one such sterically-hindered phenolic compound has a solubility in the above ranges.

Use can be made of any of a wide variety of inert organic processing solvents that can be vaporized at a temperature below the lowest melting point or melting range of the particulate components being used. For example, if the lowest component melts, say, at 55° C., the processing solvent used should be capable of being totally vaporized at a temperature below 55° C., preferably at ambient atmospheric pressure. If necessary or desirable, however, the drying can be performed at reduced pressure as long as the vacuum applied does not result in appreciable decompaction of the shaped granules.

Non-limiting examples of types of processing solvents which can be used include hydrocarbons, e.g., alkanes, cycloalkanes, alkenes, cycloalkenes, and aromatic hydrocarbons; halogenated hydrocarbons; ethers; alcohols; and ketones. A few illustrative examples of such solvents include pentane, hexane, isopentane, heptane, isohexane, 2-methylheptane, cyclopentane, cyclohexane, methylcyclopentane, methylcyclohexane, benzene, toluene, chloroform, methylene chloride, diethyl ether, 2-ethyoxypropane, tetrahydrofuran, 1,4-dioxane, ethyl alcohol, isopropyl alcohol, acetone, methylethyl ketone, and mixtures thereof. Preferred are hexane, isohexane, and cyclohexane.

In cases where all of the particulate components have melting points or initial melting temperatures significantly above 150° C., e.g., 180° C. or above, it is nevertheless preferable to use a processing solvent that is an inert organic solvent that can be completely vaporized at a temperature below about 150° C. and atmospheric pressure. While it is possible in such cases to use inert processing solvents which have boiling points or final boiling temperatures above 150° C. at atmospheric pressure, such higher boiling solvents may require use of more expensive drying methods and equipment, such as vacuum drying, depending upon the melting points or lowest melting temperature of the particulates being processed. Moreover, unless carried out under suitably controlled conditions, some decompaction of the wet compressed granules may occur during vacuum drying.

During the granulation process, the phenolic component, the other particulate polymer additive(s), and the processing solvent are converted into a substantially uniform paste. It is preferable that the paste be of a consistency that it can be extruded without need for excessively high operating pressures, or temperatures that would result in melting and/or fusion. The granulation process should thus be conducted such that if the wet paste is worked and extruded through a die press, the internal temperatures of the apparatus and of the paste are kept below temperatures at which melting and fusion of the particles may occur. Suitable ways of conducting operations in this manner are of course well-known to those of ordinary skill in the art.

Any proportions of the selected particulate additive components of (a) and (b), and processing solvent that form a compressible or compactible and shapeable paste without melting any component can be used. Without in any way limiting the range of proportions for use in forming suitable pastes, in general, it is preferable to have a solvent:total additive weight ratio in the range of from about 3 to about 20 parts by weight of solvent per 100 parts by weight of total additive. By total additive is meant all of the particulate additives being used in forming the paste and resultant granules or pellets.

One or more granulation methods maybe used to form the paste (solvent-wet additive powder mixture) into granules. One of the most convenient methods is to extrude the paste through a die plate with suitable-sized holes to produce one or more strands or "noodles" which are sliced into pellets of desired length. Such pellets are typically cylindrical with a cross section size and shape determined by the characteristics of the holes in the die plate. The cross sectional shape of the pellet generally does not greatly affect its compressive hardness, and thus does not greatly affect the dusting properties of the granular mixture. A wide range of cross sectional shapes can be used. Suitable cross sectional shapes include circular, oval, triangular, rectangular, pentagonal, hexagonal, other polygonal, and semicircular and other shapes with one or more curved sides. It is preferable that the cross sectional area be in the range of from about 1 to about 75 square millimeters. More preferable is a cross sectional area in the range of from about 3 to about 20 square millimeters. A cross sectional area in the range of from about 3 to about 9 square millimeters is most preferable. A pellet length distribution in the range of from about 0.5 to about 10 times the effective pellet diameter is desirable, with a pellet average length in the range of from about 1 to about 5 times the pellet diameter being desirable, and a pellet average length in the range of from about 2 to about 3 times being most desirable. By "effective pellet diameter" is meant the maximum cross-sectional dimension of the pellet. For example, in the case of cylindrical pellet, the effective pellet diameter is the diameter of its circular cross section, whereas in the case of a square pellet the effective pellet diameter is the diagonal distance of its square cross-section from one corner to the opposite corner.

The formation of cylindrical pellets is convenient and thus preferred. However, other methods of granulation can be used instead of or in addition to die-plate formed cylindrical pellets. For example, a Marumerizer (LCI Corporation) can be used to convert cylindrical pellets into pellets which are roughly spherical. The preferred, more preferred and most preferred cross sectional areas of pellets produced this way are as for extruded pellets as described above.

The granules produced by the process of this invention typically have the benefit of having extremely low dust-forming characteristics. However, since the granulation process itself may in some cases produce some broken granules or other dust-producing fines, it is desirable in such cases to remove particles smaller than about 0.25 millimeter in size. This can be readily accomplished by sieving the dry granules with a screen having 0.25-millimeter openings, such as a U.S. Standard No. 60 screen. Other suitable methods of classifying the granules to remove these small particles can be used, if desired. Where low dusting is of importance to the user of the granules, it is desirable that the granules contain at most about 3 wt % of particles smaller than 0.25 millimeter. Preferred low-dust granules of this invention contain no more than about 0.5 wt %, and more preferably no more than about 0.1 wt %, of particles smaller than 0.25 millimeter.

The compression or compaction and shaping of the paste into granules or pellets is preferably conducted in a pellet mill, a device which typically kneads the contents with rollers and forces the contents through orifices of a die. The pellet mill will typically be operated at a die temperature in the range of from about ambient room temperature (e.g., about 20° C.) up to about 5° C. below the boiling temperature of the processing solvent being used, which in turn is below the lowest melting temperature of any of the particulates in the paste. For example if the processing solvent used is cyclohexane (bp=81° C.), the die temperature should typically be in the range of about 20 to about 76° C. To ensure that at least some of the processing solvent remains in the pellets as they are being shaped or formed, the pellet mill is preferably operated at a die temperature that is at least about 10° C. below, and more preferably at least about 20° C. below, the normal boiling temperature of the processing solvent. As there typically are no external or internal heaters or electrical or electronic temperature controllers in a pellet mill, the balance between the frictional heating rate from the flow of paste through the die orifices and the natural heat losses from the pellet mill sets up the actual die temperature for a given paste composition. In practice, the desired die temperature is achieved by appropriately setting two principal operating variables for a given composition: 1) The concentration of processing solvent (die temperature decreases with increasing solvent concentration), and 2) the aspect ratio (i.e., working length—also called "pressway" length—divided by the diameter of the die holes). Die temperature typically increases with increasing aspect ratio. Other operating parameters of the pellet mill (e.g., rotor speed, paste feed rate, etc.) can also affect die temperature, but these normally have a relatively small effect on the die temperature compared with the solvent concentration in the paste and the aspect ratio of the die holes.

Other types of equipment which may be used for compressing or compacting and shaping the paste into granules or pellets include paste extruders and powder extruders. These devices typically operate in similar fashion to pellet mills except that they utilize rotary screw action to force the contents through the die holes rather than using rollers for this purpose.

In the practice of this invention the temperatures of the paste being compressed or compacted and shaped must not be above the melting temperature of the granules or pellets or of any of the solid additive component(s) therein.

It will be understood and appreciated that the compression or compaction and shaping can be conducted in either order. Thus, it is possible to shape the wet paste into large granular form and then subject these large granules to compression to form the compacted granules. However, typically the wet paste will be compressed such as by extrusion through a die orifice and then shaped into granules by cutting the extrudate.

In the solvent-wet mixture prior to granulation, it is preferable that the weight percent of processing solvent in the wet paste mixture be in the range of from about 1 to about 20 wt % and preferably in the range of from about 2 to about 10 wt %. Most preferably the wet paste mixture prior to granulation contains in the range of about 5 to about 10 wt % of processing solvent.

The granules can vary in the relative proportions of component(s) (a) to component(s) (b). For example, these components can be used in an (a):(b) weight ratio as high as about 99.9:0.1, but usually such ratio will be up to about 50:50, and typically in the range of about 3:97 to about 40:60. Preferably such (a):(b) weight ratio is in the range of about 5:95 to about 30:70, and most preferably in the range of about 15:85 to about 30:70. In one embodiment of this invention all of the solids in the granules are particles of (a), i.e., one or more sterically-hindered phenolic compounds, wherein the particles in said composition are held together in compacted dry granular form exclusively or substantially exclusively by contact with dried surfaces of in situ desolvated particles from particles of one or more at least partially solvated components of (a), and optionally by contact with dried surfaces of in situ desolvated particles from particles of one or more at least partially solvated components of (b).

Prior to use or storage, the granules or pellets must be dried of all or nearly all of the processing solvent. Amounts of residual solvent, if any, will typically be trace amounts, e.g., up to about 100 ppm wt/wt of residual processing solvent. The drying process can take place at room temperature or at an elevated temperature, with temperatures in the range of from about 60° C. to about 105° C. being most convenient, provided of course that the drying temperature is not above the melting temperature of the granules or of any of the additive component(s) therein. Many types of dryers are suitable, such as a forced air oven, vacuum oven, fluid bed dryer, Wyssmont dryer or belt dryer. It will be understood, of course, that the wet compressed granules need not be under a compressive force that is being applied at the time the granules are being dried. It will also be understood that the dried granules consist essentially of components (a) and (b) modified only to the extent, if any, that salvation, desolvation, and compression may affect their original physical condition and/or chemical composition. Generally speaking, no components other than components (a) and (b) and the processing solvent are present in the pastes used in forming the dried granular compositions of this invention. If it is desirable to include a liquid as a polymer additive in the compositions of this invention, it should form a single phase liquid with the processing solvent and not adversely affect the processing of the paste or the properties of the dried granules. In addition, any such liquid used as a polymer additive should be devoid or substantially devoid of any binding properties and must be capable of being dried under the drying conditions used in forming the dried compacted granules. Ordinarily no more than about 20 wt % of the finished dried granules should be based on dried residue from such dried, non-binding, initially liquid polymer additive.

A suitable index of the tendency of a granular material to produce dust is the compressive hardness of the particles. The term "compressive hardness" as used herein is defined as a measure of the friability resistance of the granule as determined by:
1) placing the granule between two parallel, unpadded steel plates such that the long dimension of the pellet is parallel to the steel plates;
2) applying an increasing load to the top plate while holding the bottom plate stationary until the pellet begins to disintegrate; and
3) dividing the load obtained in step 2) by the length of the granular test specimen.

Compressive hardness is generally expressed in units of lbs/in. Generally, a granule with a high compressive hardness has only a low tendency towards dust production, whereas a low compressive hardness indicates strong tendency to produce dust. Good friability resistance characteristics are obtained with a compressive hardness greater than about 5 lbs/in, with greater than 10 lbs/in being more preferred, and greater than 15 lbs/in being most preferred. In conducting this procedure one should randomly select at least 13 particles from a given batch of dried granules, subject each such particle individually to the procedure, and calculate the average compressive hardness value from the results on each of the 13 or more individual particles tested.

When forming or shaping the granules such as pellets according to the process of this invention, it is preferable in most cases that the phenolic component be partially but not completely dissolved in the processing solvent. However in some cases, for example where the proportion of the phenolic component in the blend of (a) plus (b) is relatively small (e.g., in amounts in the vicinity of about 3 to about 5 wt %), it can be advantageous for all of the phenolic component to be in solution. Examination of dried granules of this invention by scanning electron microscopy (SEM) typically shows that the particles are closely packed together—dried glue or adhesive, if any, formed in the process is usually not readily perceivable by SEM. In situations where essentially complete solvation followed by desolvation of the phenolic component has occurred, the particles of the desolvated phenolic component in the dried granules may be irregularly-shaped and of different sizes from their original size before use in the process. It is to be clearly understood and appreciated that these characteristics relating to SEM observations are not to be construed as limitations or requirements of the invention. As long as partial solvation of at least the phenolic component occurs in the process and the solvated portion of at least the phenolic component is dried while the particles in the granules are in intimate compacted contact one to another, the resultant dried granules of this invention exhibit the compressive hardness and physical integrity to be used in conventional dry blending operations.

The following Examples illustrate this invention, but do not limit its scope. In Examples 1-5 processability testing or pellet hardness measurements to determine the processability characteristics of the pellets, i.e., hardness and attrition resistance was determined by subjecting the pellets to manual manipulation so as to observe the friability of the pellet. In Examples 6-10 the compressive hardness test described above was used to assess the processability and physical integrity of the pellets.

EXAMPLE 1

4000 Grams of 1,3,5-trimethyl-2,4,6-tris(3,5-di-tert-butyl4-hydroxybenzyl)benzene (ETHANOX® 330 antioxidant obtained from Albemarle Corporation) and 444 grams of anhydrous acetone were combined in a Kahl Model KDHJ-20 batch kneader and then blended for about 3 minutes. The resulting pasty powder blend was then transferred to a polyethylene bag, the bag was sealed and the material was stored for about 15 minutes. The blend was then manually fed to a Kahl Model 14-175 pellet mill operating at 100 rpm and equipped with a die plate having 2 mm diameter holes and a 6 mm pressway length. The pelletized product was then dried in a 200° F. (ca. 93° C.) oven for about 2 hours to yield a product consisting of 94% pellets and 6% fines (−20 mesh particles). The resulting pellets were relatively very hard, in the sense that considerable force was required to break them down into powder when subjected to manual compression and therefore could be handled with typical conveying equipment with minimal attrition. For comparative purposes neat ETHANOX® 330 antioxidant powder was processed on a pellet mill operating under the same conditions as above described but in which no acetone was introduced. The products from the pellet mill consisted of nearly all powder with a few very soft pellets. This comparative example illustrates that the processing solvent such as acetone of the instant invention is necessary to impart the desired hardness to the pellets.

EXAMPLE 2

Fourteen batches of feed material were prepared as follows: 1.33 kg of ETHANOX® 330 antioxidant powder and 2.67 kg of tris(2,4-di-tert-butylphoshite (Irgafos 168 powder) (obtained from Ciba Specialty Chemicals Corporation) were combined in a Kahl model KDHJ-20 batch kneader then dry blended for 5 minutes. 571 Grams of acetone was added to the powder in the kneader and blending was then continued for an additional 3 minutes. The resulting pasty solid blend was discharged from the kneader into a polyethylene bag which was then sealed. The fourteen batches of feed material were then manually fed to a Kahl Model 33-390 pellet mill operating at 80 rpm speed and equipped with a die plate having 3 mm diameter holes and a pressway length of 9 mm. The product obtained from the pellet mill was dried in a 200° F. (ca. 93° C.) oven for about two hours. Dry sieving of the dried product with a US Standard mesh screen indicated that the product consisted of 95.8% pellets (+12 mesh) and 4.2% fines (−12 mesh). The dried pellets exhibited adequate hardness and thus were judged suitable for handling with conventional conveying equipment without significant attrition.

EXAMPLE 3

A pelletized blend composition consisting of ETHANOX® 330 antioxidant blended with Irgafos® 168 secondary phosphite antioxidant, dihydrotalcite from Kyowa Chemical Company and glycerol was prepared as follows: 2.63 kg of ETHANOX® 330 antioxidant, 1.215 kg of Irgafos® 168 and 0.790 kg of dihydrotalcite were combined in a Kahl Model KDHJ-20 batch kneader and dry blended for 5 minutes. 0.263 kg of glycerol and 0.556 kg of anhydrous acetone were added to the kneader and blending was continued for an additional 3 minutes. The pasty mass from the kneader was transferred to a polyethylene bag for about 15 minutes storage. The mass was then manually fed to a Kahl Model 14-175 pellet mill operating at 100 rpm and equipped with a die plate having 3 mm diameter holes and a pressway length of 9 mm. The product from the pellet mill was collected and dried at 200° F. (ca. 93° C.) for about 2 hours. The dried product consisted of 93.9% pellets and only 6.1% fines (i.e., −12 mesh particles). The dried pellets were subjected to manual characterization and judged to have very good hardness and therefore good resistance to particle attrition during pellet conveying operations.

EXAMPLE 4

The procedure of Example 3 was repeated with half of the acetone processing solvent replaced with isopropyl alcohol. The resulting pellets were determined to be not as hard as those obtained in Example 3 but the hardness through manual characterization was judged to be sufficient to impart sufficient attrition resistance in the pellet conveying operation while exhibiting sufficient softness to permit the ready dispersion of the antioxidant pellet in to a host polymer.

EXAMPLE 5

The procedure of Example 3 was repeated with the 0.556 kg of anhydrous acetone replaced by 0.319 kg of methylethyl ketone. The dried pellets were subjected to manual characterization and judged to have very good hardness and therefore good resistance to particle attrition during pellet conveying operations. This Example also illustrates that methylethyl ketone may be employed at relatively low concentrations in the process of this invention and, therefore, is a preferred solvent in terms of the economics of carrying out the process.

EXAMPLE 6

A blend of tetrakis[methylene(3,5-di-tert-butyl-4-hydroxyhydrocinnamate)]methane (Irganox 1010 hindered phenol antioxidant powder) (100 parts by weight) and methylethyl ketone processing solvent (10 parts by weight) was prepared in a tumble blender, then transferred to a K-Tron twin screw volumetric feeder. The blended powder/solvent mixture was shaped into cylindrical pellets with a Kahl Model 14-175 pellet mill (LCJ Corp.), which was equipped with a die plate having circular cross-section holes of 3 mm diameter by 9 mm pressway length, operated at nominally 100 rpm rotor speed, and fed with the powder/solvent mixture at a rate of about 32-40 lb/hr. During the pelleting operation, the die plate temperature was in the range of about 37 to about 53° C. The raw wet product output of the pellet mill was collected in stainless steel trays, which were placed in a forced air oven, operating at 90° C. and under nitrogen purge, for about 4 hours to remove the processing solvent. The dried product was sieved with a US Standard No. 8 screen to remove the processing fines (i.e., the −8 mesh material), which comprised about 1% by weight of the dried product. The finished product (+8 mesh material) consisted of bone-white cylindrical pellets having a diameter of nominally 3 mm, an average length of about 12 mm, and a compressive hardness of 15 lb/in (average of hardness measurements on 13 individual pellets).

EXAMPLE 7

A blend of Irganox 1010(10 parts by weight), Ultranox 627A antioxidant (3 parts by weight), and cyclohexane processing solvent (1.3 parts by weight) was prepared in a tumble blender by: 1) combining the Irganox 1010 and Ultranox 627A powders in a tumble mixer and blending the mixture for 6 minutes, 2) adding the processing solvent to the blended powder and blending for 6 minutes. The powder/processing solvent mixture was shaped into cylindrical pellets with a Kahl Model 14-175 pellet mill, which was equipped with a die plate having circular cross section holes of 3 mm diameter by 9 mm pressway length, operated at nominally 100 rpm rotor speed, and fed with the powder/processing solvent mixture at a rate of 61-69 lb/hr. During the pelleting operation, the die temperature was in the range of about 40 to about 60° C. The wet output of the pellet mill was dried and then sieved to remove the fines (about 2% by weight) as in Example 6. The finished product pellets consisted of bone-white cylindrical pellets having a diameter of nominally 3 mm, an average length of about 7 mm, and a compressive hardness of 21 lb/in.

EXAMPLE 8

A blend of Irganox 1010(5 parts by weight), Irgafos 168(5 parts by weight), DHT-4A (2 parts by weight), and cyclohexane processing solvent was blended, pelletized, dried, and sieved per the procedures of Example 7 but with the following changes in operating conditions: 1) The pressway length of the die plate was 10.5 mm, 2) the feed rate of powder/processing solvent mixture to the pellet mill was 91-97 lb/hr, 3) the die temperature was in the range of about 52 to about 62° C., 4) the drying was performed at 93° C. for about 2.7 hr. About 2.5% by weight of the dried material was removed as fines (−8 mesh material) by the sieving operation to give the finished product pellets, which consisted of bone-white cylindrical pellets having a diameter of nominally 3 mm, an average length of about 7 mm, and a compressive hardness of 21 lb/in.

EXAMPLE 9

Example 8 was essentially repeated but with the following changes: 1) Hexane was substituted for the cyclohexane processing solvent, 2) the feed rate of powder/hexane mixture to the pellet mill was about 85-125 lb/hr, and 3) the temperature of the die plate was in the range of about 42 to about 48° C. About 3% by weight of the dried material was removed as fines (−8 mesh material) to give the finished product pellets, which consisted of bone-white cylindrical pellets having a diameter of nominally 3 mm, an average length of about 7 mm, and a compressive hardness of 16 lb/in.

EXAMPLE 10

Example 8 was essentially repeated but with the following changes: 1) methylethyl ketone was substituted for the cyclohexane processing solvent, 2) the feed rate of the powder/methylethyl ketone mixture to the pellet mill was about 60-70 lb/hr, and 3) the temperature of the die plate was in the range of about 40 to about 45° C. About 1% by weight of the dried material was removed as fines (−8 mesh material) to give the finished product pellets, which consisted of bone-white cylindrical pellets having a diameter of nominally 3 mm, an average length of about 7 mm, and a compressive hardness of 14 lb/in.

Examples 1-10 demonstrate that the desolvated, dried, formerly at least partially solvated phenolic component serves as a highly effective binding component to hold the particles together after compression and drying, thus eliminating the need for conventional binders or melted components in forming granules such as pellets having desirable physical integrity.

Accordingly, it can be seen that in the practice of this invention, polymer additive compositions are produced and provided in granular form without use of any melted component such as a low melting binder or and component that in its non-wet state is sticky or pliable (putty-like). Likewise polymer additive compositions are produced and provided in granular form without requiring use of fatty acids or fatty alcohols or their derivatives such as metal stearate salts (e.g., calcium stearate, magnesium stearate, zinc stearate, etc.). However it is possible, though not preferred, to include such salts in the compositions of this invention to partake of their acid neutralizing capability, provided that they do not interfere with the bonding brought about by the desolvated, dried, formerly at least partially solvated phenolic component of (a) used in the practice of this invention, and provided further that their presence does not adversely affect the particular polymer in which the granules are to be employed.

It can further be seen that the compacted particulate polymer additive compositions of this invention are composed of integral granules formed from packed-together particles which, while at least partially solvated, were dried while in intimate contact one to another.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

It will also be understood that the terms "substantial" and "substantially" denote that chemical processes or operations ordinarily do not involve absolutes. According to a standard dictionary definition which is relied upon herein, "substantial" means being of considerable importance, value, degree, amount, or extent. Such a definition is certainly clear enough to be readily understood by anyone having ordinary skill in the scientific arts. Thus instead of describing a variable as an absolute, it is far more realistic to describe the variable as being in the substantial vicinity of the expressed variable. For example when describing whether melting occurs it is possible that an inconsequential number of molecules of a substance may melt without such melting having any detectable or significant effect upon the result being achieved. Thus it is far more realistic to indicate that melting is prevented or substantially prevented so as to avoid hypertechnical legalistic manipulation of words. Thus in any and all respects, this document should be read with the application of reason and common sense.

It is to be understood that the reactants and components referred to by chemical name or by formula anywhere in the specification or claims hereof, whether referred to in the singular or plural, are identified as they exist prior to coming into contact with another substance referred to by chemical name or chemical type (e.g., another component, a solvent, or etc.). It matters not what preliminary chemical changes, chemical transformations and/or chemical reactions, if any, take place in the resulting mixture or solution as such changes, transformations and/or reactions are the natural result of bringing the specified components together under the conditions called for pursuant to this disclosure. In short, the components are identified as ingredients to be brought together in connection forming a mixture to be used in conducting specified operations. In addition, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure.

Each and every document cited herein is incorporated into this disclosure as if set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of producing a compacted particulate polymer additive composition in a dry granular form, which process comprises:
   1) forming a paste from (a) at least one particulate sterically-hindered phenolic compound, (b) one or more particulate polymer additives other than a sterically-hindered phenolic compound, and (c) an inert organic processing solvent that can be vaporized at a temperature below the lowest melting point or initial melting temperature of (a) and (b);
   2) compressing and shaping the paste while preventing or substantially preventing melting of solids used in forming the paste, to produce a wet compacted composition in granular form; and
   3) drying said wet compacted composition in granular form by vaporizing said processing solvent therefrom to form the dried compacted particulate polymer additive composition in a granular form; with the proviso that the paste of 1) is devoid of any extraneous component serving as a binder.

2. A process of claim 1 wherein said paste is compressed in a compression apparatus operated so as to prevent or substantially prevent melting of solids.

3. A process of claim 1 further comprising separating fine particles from the dried compacted particulate polymer additive composition in a granular form.

4. A process of claim 1 wherein said paste is compressed in a compression apparatus operated so as to prevent or substantially prevent melting of solids, and wherein fine particles are separated from the dried compacted particulate polymer additive composition in a granular form.

5. A process of claim 1 wherein (a) and (b) have melting points or initial melting temperatures of at least about 100° C.

6. A process of claim 1 wherein (a) and (b) have melting points or initial melting temperatures of at least about 150° C.

7. A process of claim 1 wherein (a) used is at least one phenolic compound containing at least one hydroxyphenyl moiety in which at least one of the ortho-positions relative to the hydroxyl group is substituted by a tertiary alkyl group.

8. A process of claim 1 wherein (a) used is 1,3,5-trimethyl-2,4,6-tris(3,5-di-tert-butyl-4-hydroxybenzyl)benzene or 1,3,5-trimethyl-2,4,6-tris(3,5-di-tert-butyl-4-hydroxybenzyl)isocyanurate.

9. A process of claim 1 wherein each polymer additive of (b) used has a melting point or initial melting temperature of at least about 50° C. and wherein at least one said polymer additive of (b) is an organic phosphite or an organic phosphonite antioxidant, a nucleating agent, a polymer clarifying agent, an acid neutralizer or a UV or light stabilizer, a mixture of any two or more of these polymer additives.

10. A process of claim 9 wherein (a) used is at least one phenolic compound containing at least one hydroxyphenyl moiety in which at least one of the ortho-positions relative to the hydroxyl group is substituted by a tertiary alkyl group.

11. A process of claim 9 wherein (a) used is 1,3,5-trimethyl-2,4,6-tris(3,5-di-tert-butyl-4-hydroxybenzyl)benzene or 1,3,5-trimethyl-2,4,6-tris(3,5-di-tert-butyl-4-hydroxybenzyl)isocyanurate.

12. A process of claim 1 wherein (b) is selected from the group consisting of (i) at least one nucleating agent, (ii) at least one polymer clarifying agent, (iii) at least one acid neutralizer, and a mixture of any two or all three of (i), (ii), and (iii), and wherein each said component (b) used has a melting point or initial melting temperature of at least about 100° C.

13. A process of claim 12 wherein (a) used is at least one phenolic compound containing at least one hydroxyphenyl moiety in which at least one of the ortho-positions relative to the hydroxyl group is substituted by a tertiary alkyl group.

14. A process of claim 12 wherein (a) used is 1,3,5-trimethyl-2,4,6-tris(3,5-di-tert-butyl-4-hydroxybenzyl)benzene or 1,3,5-trimethyl-2,4,6-tris(3,5-di-tert-butyl-4-hydroxybenzyl)isocyanurate.

15. A process of claim 1 wherein (b) is selected from the group consisting of (i) sodium benzoate, (ii) 1,3:2,4-bis(3,4-dimethylbenzylidene)sorbitol, (iii) 1,3:2,4-bis(p-methylbenzylidene)sorbitol, (iv) 1,3:2,4-di-O-benzylidenesorbitol (v) at least one metal oxide acid neutralizer, (vi) at least one metal carbonate acid neutralizer, (vii) at least one natural or synthetic hydrotalcite, (viii) at least one organic phosphite or at least one organic phosphonite, and (ix) a mixture of any two or more of (1) through (viii) inclusive.

16. A process of claim 15 wherein (a) used is at least one phenolic compound containing at least one hydroxyphenyl moiety in which at least one of the ortho-positions relative to the hydroxyl group is substituted by a tertiary alkyl group.

17. A process of claim 15 wherein (a) used is 1,3,5-trimethyl-2,4,6-tris(3,5-di-tert-butyl-4-hydroxybenzyl)benzene or 1,3,5-trimethyl-2,4,6-tris(3,5-di-tert-butyl-4-hydroxybenzyl)isocyanurate.

18. A process of claim 1 wherein component (a) used is 1,3,5-trimethyl-2,4,6-tris(3,5-di-tert-butyl-4-hydroxybenzyl)benzene or 1,3,5-trimethyl-2,4,6-tris (3,5-di-tert-butyl-4-hydroxybenzyl)isocyanurate, and wherein component (b) used is tris(2,4-di-tert-butylphenyl)phosphite or bis(2,4-di-tert-butylphenyl)pentaerythritol diphosphite.

19. A process of claim 2 wherein component (a) used is 1,3,5-trimethyl-2,4,6-tris(3,5-di-tert-butyl-4-hydroxybenzyl)benzene or 1,3,5-trimethyl-2,4,6-tris(3,5-di-tert-butyl-4-hydroxybenzyl)isocyanurate, and wherein component (b) used is tris(2,4-di-tert-butylphenyl)phosphite.

20. A process of claim 2 wherein component (a) used is 1,3,5-trimethyl-2,4,6-tris(3,5-di-tert-butyl-4-hydroxybenzyl)benzene or 1,3,5-trimethyl-2,4,6-tris (3,5-di-tert-butyl-4-hydroxybenzyl)isocyanurate, and wherein component (b) used is bis(2,4-di-tert-butylphenyl)pentaerythritol diphosphite.

* * * * *

UNITED STATES PATENT AND TRADEMARK OFFICE
CERTIFICATE OF CORRECTION

PATENT NO. : 7,425,290 B2
APPLICATION NO. : 10/911253
DATED : September 16, 2008
INVENTOR(S) : John Semen It is certified that error appears in the above-identified patent and that said Letters Patent is hereby corrected as shown below:

Column 8, the structure on lines 26-35 is shown as:

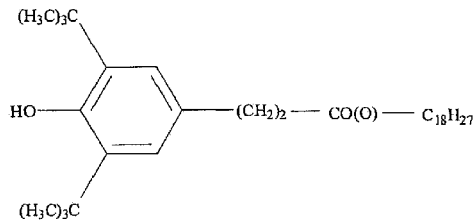

and should be shown as:

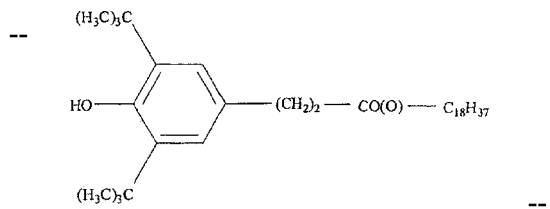

Column 8, lines 40-62 reads "B. Tetrakis[methylene(3,5-di-t-butyl-4-hydroxylhydrocinnamate)] methane having the structure:

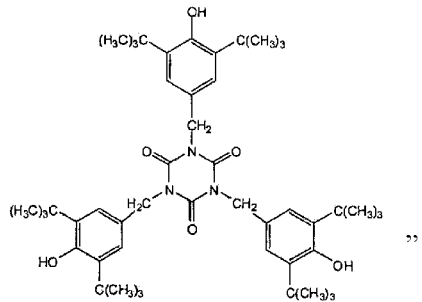

"

Signed and Sealed this

Thirty-first Day of August, 2010

David J. Kappos
*Director of the United States Patent and Trademark Office* and should read -- B. Tetrakis[methylene(3,5-di-t-butyl-4-hydroxyhydrocinnamate)]methane having the structure:
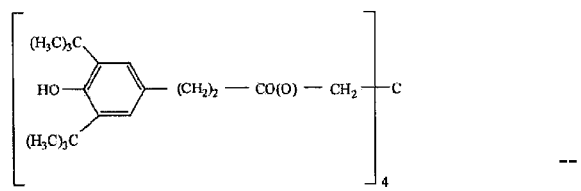
--
Column 9, structure on lines 3-14 is shown as:
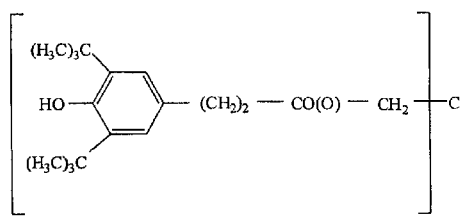
and should be shown as:
--
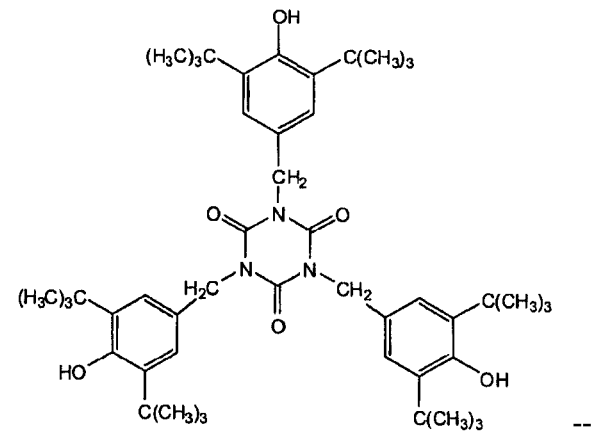
--
Column 12, line 51 reads "SAYTEX 801" and should read -- SAYTEX® 8010 --
Column 12, line 67 reads "(3 mbH)" and should read -- GmbH) --